United States Patent [19]
Blecher

[11] 3,957,653
[45] May 18, 1976

[54] APPARATUS FOR COLLECTION, SEPARATION AND ISOLATION OF BLOOD

[75] Inventor: Jacob B. Blecher, Fair Lawn, N.J.

[73] Assignee: Becton, Dickinson and Company, East Rutherford, N.J.

[22] Filed: Apr. 3, 1975

[21] Appl. No.: 564,646

[52] U.S. Cl. ................................ 210/518; 215/6; 215/306; 210/DIG. 23; 220/23; 233/1 A
[51] Int. Cl.² ...................................... B01D 21/26
[58] Field of Search .............. 23/258.5; 106/287 SB; 128/2 F, 214 R, 218 M, 272; 210/65, 83, 84, 512, 514–518, DIG. 23; 233/1 A, 1 R, 26; 215/6, 306; 220/23, 254, 255

[56] References Cited
UNITED STATES PATENTS

| | | | |
|---|---|---|---|
| 3,115,460 | 12/1963 | McCormick | 220/23 X |
| 3,167,079 | 1/1965 | Weil | 220/23 X |
| 3,199,707 | 8/1965 | Folkman | 215/306 |
| 3,367,484 | 2/1968 | Nelson | 220/23 X |
| 3,780,935 | 12/1973 | Lukacs | 210/83 X |
| 3,852,194 | 12/1974 | Zine, Jr. | 210/DIG. 23 |

*Primary Examiner*—Charles N. Hart
*Assistant Examiner*—Robert H. Spitzer
*Attorney, Agent, or Firm*—Kane, Dalsimer, Kane, Sullivan and Kurucz

[57] ABSTRACT

Disclosure is made of a novel apparatus for the collection, separation and isolation of serum or plasma from blood obtained from mammalian capillary sources. The apparatus comprises a tubular blood collection component and an airtight closure therefor. The closure member includes a reservoir and means of dispensing a thixotrope into the blood collection chamber, under centrifugal force, to effect a physical separation and isolation of the desired serum or plasma. The apparatus is advantageously employed to minimize loss of blood gases during separation and holding.

3 Claims, 3 Drawing Figures

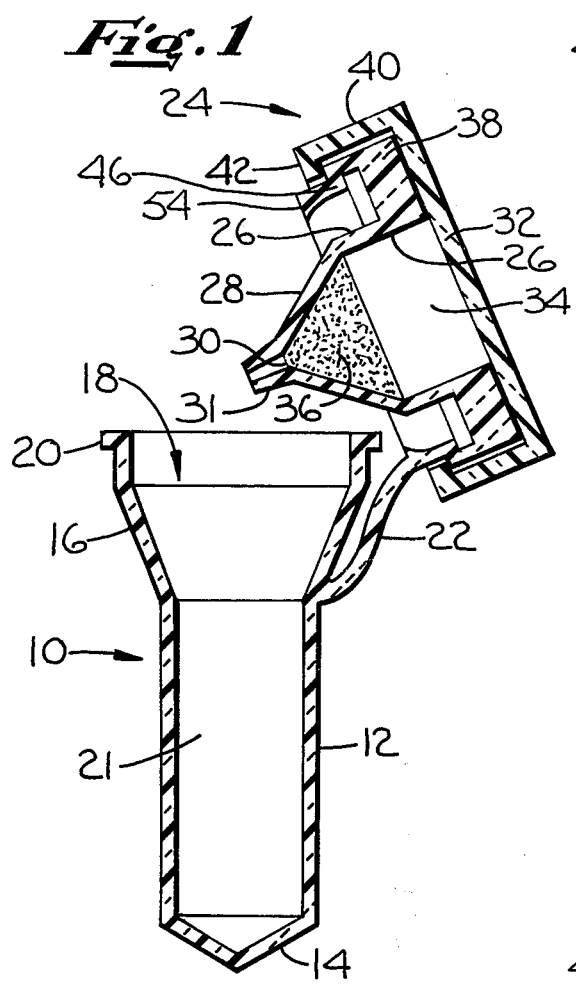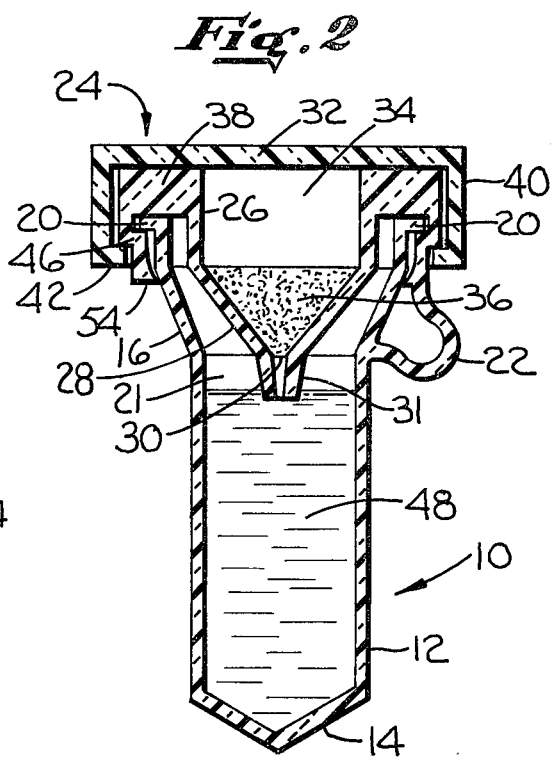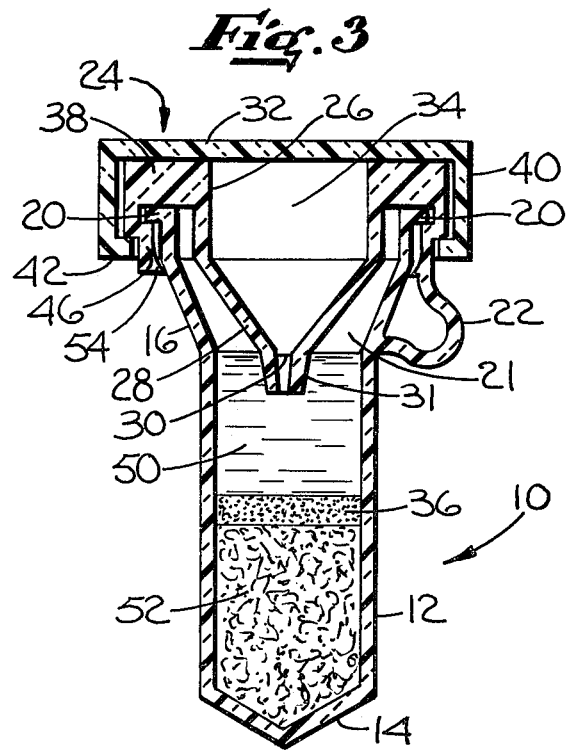

APPARATUS FOR COLLECTION, SEPARATION AND ISOLATION OF BLOOD

BACKGROUND OF THE INVENTION

1. Field of the Invention

The invention concerns apparatus for the collection, separation and isolation of blood and more particularly concerns apparatus for the centrifugal separation of blood into its component liquid and solid portions.

2. Brief Description of the Prior Art

Advances in modern analytical instrumentation have made it possible to carry out a variety of hematological, chemical and toxicological diagnostic procedures on very small quantities of blood. This is an advantageous advance since it obviates the need to withdraw venous blood from a patient. Instead, sufficient quantities of blood may now be obtained by the less traumatic procedure of collecting capillary source blood from a finger tip, ear lobe, and the like.

Prior to my invention, the most widely used means for collecting capillary blood has been by employment of the standard capillary tube. However, collection of blood specimens in capillary tubes requires a fair degree of technical proficiency on the part of medical personnel if air pockets within the capillary collector are to be avoided. Furthermore, capillary tubes are relatively fragile and subject to ready breakage. For the storage of relatively large quantities of blood, several capillary tubes must be employed. In addition, capillary tubes are not generally suitable vessels for the blood if it is to be separated into its serum and solids components while therein. Further, blood stored therein is often difficult to remove since the blood will often clot and clog the capillary even if treated with an anticoagulant.

Although the need for an improved apparatus for the collection, separation and isolation of capillary blood has been evident for a number of years, there have been few attempts to satisfy this need.

Prior to this invention, apparatus for the collection of capillary blood was known; see for example copending application Ser. No. 400,882 filed Sept. 26, 1973. However, such apparatus functions to collect and separate capillary blood into its component serum or plasma and solids portions only. It cannot function to effect a sealed isolation of the blood components from each other.

U.S. Pat. Nos. 3,780,935 and 3,852,194 disclose methods and apparatus for the sealed isolation of blood plasma or serum from the solid constituents of blood, by centrifugal force emplacement of a thixotrope sealant barrier between the centrifugally separated blood components. However, the apparatus of these latter disclosures have not been found satisfactory for use in the collection, separation and isolation of serum or plasma from capillary blood because they are not suitable for use with relatively small volumes of blood.

In general, the collection, separation and isolation of serum or plasma from capillary blood has posed problems not associated with the collection, separation and isolation of blood obtained from mammalian venous and arterial sources. For example, the prior art devices are generally inadequate for protecting very small volumes of capillary blood from contamination by airborne contaminants and from loss of gaseous materials normally dissolved in blood serum or plasma, between collection of the blood and its processing to isolate the serum or plasma.

The apparatus of my invention fulfills the needs of the art and provides a means for the efficient collection, separation and isolation of serum or plasma from capillary blood while protecting the isolate from exposure to contaminants or loss of gases normally dissolved in the serum or plasma.

SUMMARY OF THE INVENTION

The invention comprises apparatus for the collection, separation and isolation of serum or plasma from capillary blood, which comprises; a first tubular body having a fixedly closed end and an open end, said open end having a greater width than said closed end, said body and said open and closed ends together defining a blood collection reservoir with the capacity of from about 200 to about 1,000 microliters of blood; a first flange disposed about the outer periphery of said open end; a movable first closure member adapted to nest in and to seal said open end, said closure member comprising, a second tubular body having open upper and lower ends and which defines a sealant holding chamber, the opening in said lower end being of a dimension which is insufficient to permit the passage of a thixotrope under the force of one gravity but sufficient to permit the passage of said thixotrope under a centrifugal force; a second flange disposed about the outer periphery of said upper end; a second movable closure member for sealing said upper end, said second movable closure having means formed thereon for releasably engaging said second flange in a fluid-tight sealing association; a thixotrope sealant held in said sealant chamber, said thixotrope having a specific gravity within the range of from 1.03 to 1.09; means formed on said second flange for releasably engaging said first flange in a fluid-tight association; and means of movably attaching said first closure to said first tubular body; whereby when both of said means for releasably engaging said second flange are engaged, the contents of said apparatus are hermetically sealed therein.

BRIEF DESCRIPTION OF THE DRAWINGS

FIG. 1 is a cross-sectional side elevation of an embodiment of the invention.

FIG. 2 is a cross-sectional side elevation of the embodiment of FIG. 1 filled with blood.

FIG. 3 is a cross-sectional side elevation as in FIG. 2 but following separation and isolation of serum or plasma.

DETAILED DESCRIPTION OF THE INVENTION

A complete understanding of the invention may be conveniently obtained by reference to the preferred embodiment shown in the accompanying drawings of FIGS. 1–3, inclusive.

FIG. 1 is a cross-sectional side elevation of a preferred embodiment of the invention and shows apparatus 10 which consists of a tubular body 12 having a fixedly closed end 14. Body 12 also has an end 16 which is outwardly flared to provide opening 18 having a greater dimension in width than found at closed end 14. Disposed about the periphery of open end 18 there is seen a flange 20 which is integral with the tubular body 12. The flared end 16 provides a convenient cup shaped opening 18 which facilitates the collection of capillary blood from, for example, a mammalian finger tip or ear lobe. The cup shaped opening 18 assures that blood collected from a finger tip or ear lobe source will be directed inwardly and into the blood collection chamber 21 defined by body 12 with its ends 14 and 18. In the absence of a flared opening such as is shown in FIG. 1, it is difficult to collect capillary blood directly from a finger tip or ear lobe.

There are preferred dimensions for the tubular body 12. Preferably, the chamber 21 has a capacity to hold a volume of between about 200 to about 1,000 microliters of blood when closure member 24 is in place. This is the ideal volume of chamber 21 to assure minimum exposure of the capillary blood collected to air which may also be contained within the chamber 21. Preferably, the chamber 21 below flared end 16 has a width of at least 7.5 millimeters to assure that blood collected through the cup shaped opening 18 will travel under the force of gravity to the bottom of chamber 21.

Attached to the body 12 by a flexible strap type of hinge 22 there is seen a movable closure member 24 which is adapted to nest in and to seal the cup shaped opening 18 of body 12. Closure member 24 consists of a tubular body 26 which has a lesser outer diameter than found in the interior diameter of opening 18. Both upper and lower ends of tubular body 26 are open. The opening at the lower end of tube 26 is reduced by inwardly tapered portions 28 of the body 26 to provide an aperture 30 passing through nozzle 31. The nozzle 31 is of a length sufficient to extend beneath the surface of collected blood, so that thixotrope 36 as described hereinafter is deposited beneath the blood surface during subsequent centrifugation. The aperture 30 is of a dimension which is insufficient to permit the passage of a thixotrope under the force of one gravity, but of sufficient dimension to permit the passage of said thixotrope when a centrifugal force is applied to the thixotrope. A specific dimension for aperture 30 is somewhat dependent upon the degree of thixotropy in a particular thixotrope. In general, the width of aperture 30 is within the range of from about 1/32 to about 1/16 inch. Those skilled in the art will appreciate that selection of a specific width for aperture 30 can be determined by trial and error for specific thixotropes. The upper end of tubular body 26 is closed by a movable closure illustrated by snap fitting cap 32. Tubular body 26 together with its ends defines a sealant holding chamber 34. In FIG. 1, sealant holding chamber 34 contains a thixotrope 36. Thixotrope 36 is more specifically a sealant material characterized by its water insolubility, non-toxicity regarding its effect on living blood cells, chemical inertness with respect to the constituents of a blood sample, particularly as found in blood serum or plasma and an ability to maintain a rigid barrier under ordinary conditions but which will flow like a fluid when exposed to a shear force such as a centrifugal force. The thixotrope must have a specific gravity within the range of from about 1.03 to about 1.09. Preferably, the thixotrope sealant material will have a specific gravity of about 1.06. Thixotropic sealant materials 36 as described above are well known to those skilled in the art as is their preparation; see for example U.S. Pat. Nos. 3,780,935 and 3,852,194.

Disposed about the outer periphery of the upper end of tubular body 26 there is seen a flange 38. Flange 38 in cooperation with lip 42 formed on side wall 40 of the snap fitting cap 32 forms an airtight, fluid tight seal so that the open upper end of tubular body 26 is hermetically sealed.

Referring now to FIG. 2, a cross-sectional side elevation, as seen in FIG. 1 but with closure member 24 securely sealing the open end 18. With closure member 24 in place, lip 46 formed on flange 38 securely engages flange 20 of tube body 12 in an airtight, fluid tight sealing association so that when in place, closure member 24 provides a hermetic sealing of the contents within chamber 21 of tubular body 12. As shown in FIG. 2, blood 48 derived from a mammalian capillary source has been collected in chamber 21 prior to the sealing of tube 12 by closure member 24. In this state, capillary blood 48 is protected from contamination with airborne contaminants or from exposure to the atmosphere whereby a gaseous exchange could occur between atmospheric gases and gases dissolved within blood specimen 48.

Apparatus 10 may be fabricated from conventional materials normally employed in the construction of laboratory vessels. Desirably, the apparatus 10 is fabricated from materials which are inert to reaction with blood to reagents commonly employed in diagnostic procedures associated with blood. Representative of such preferred materials are polyethylene, polypropylene, polyvinyl chloride and like materials. Manufacturing techniques for fabricating the apparatus 10 are well known in the art and include for example injection molding to provide a unitary one piece construction (with the exception of cap member 32). The sealant 36 may be inserted in chamber 34 at the manufacturing facility prior to closure of chamber 34 with the snap fit cap 32.

The apparatus 10 may be conveniently operated according to the following procedure. Closure member 24 is removed from its sealing position in the mouth 18 of tubular collection component body 12 as shown in FIG. 1. A mammalian finger or ear lobe is punctured in a conventional manner to provide a source of capillary blood. The apparatus 10 with closure member 24 in the open position is placed beneath the blood source to receive blood within mouth 18. The blood descends under the force of gravity to chamber 21. Any desired amount up to about 1,000 microliters or more may be collected in chamber 21. If desired, anti-coagulants may be preplaced in chamber 21 so that upon entry of blood therein, admixture occurs and an anti-coagulant treated blood is obtained.

Upon filling chamber 21 with capillary blood, the closure member 24 which is readily accessible since it is attached to body 12 by strap hinge 22 is replaced to seal the opening 18. Referring now to FIG. 2, a blood 48 filled apparatus 10 is seen with closure member 24 hermetically sealing the mouth 18. The hermetic seal is obtained by engagement of flange 20 by lip 46 formed on the flange 38. The hermetic seal is provided by a close compression fit between flanges 20 and 38. The snap cap 32 is also compression fitted to flange 38 by the engagement of lip 42 with flange 38. Thus, as shown in FIG. 2 blood 48 is contained within chamber 21, protected from exposure to the atmosphere and its airborne contaminants and is protected from significant or substantial losses of dissolved gases which might occur if blood 48 were not contained within a hermetically sealed vessel. Blood 48 may be stored in apparatus 10 until separation is desired. Normally, if the blood is not treated with an anti-coagulant, it may be allowed to stand for at least one-half hour so that clot formation occurs, or it may be separated immediately.

In the next step of the procedure, the blood filled apparatus 10 is centrifuged to effect a centrifugal separation of the blood into its serum or plasma and its substantially solid or cellular portions. Simultaneously, under centrifugal force, the thixotrope 36 passes through aperture 30 and into the chamber 21. Since the thixotrope 36 has a specific gravity which is intermediate between that of normal serum or plasma and that of the substantially cellular portion of blood, it will migrate to the interface between the separated blood components. As shown in FIG. 3, a cross-sectional side elevation of the blood filled apparatus as seen in FIG. 2 but after completion of centrifugation, it is seen that thixotrope 36 has egressed from chamber 34 and now lies at the interface between serum 50 and the substantially cellular portion 52 of the blood. The thixotropic material flowed under centrifugal stress to its density gradient level between the blood components where it comes to rest and again assumes a rigid thixotropic structure, acting as a barrier between the separated blood components. It will be noted that the entire separation and isolation of the blood serum or plasma 50 was carried out with the apparatus 10 without its being opened to expose the blood specimen to the atmosphere.

Following isolation of the blood serum or plasma 50 from the substantially solid portion 52 of the blood, the entire apparatus may serve as a storage vessel until such time as transfer of the serum or plasma 50 for diagnostic purposes is desired. This storage is of course carried out without exposing the blood serum or plasma 50 to the atmosphere. When access to the desired blood serum or plasma 50 is desired, one may open and remove closure member 24 by pulling on lip 46 and swinging closure member 24 out of the mouth 18 of tubular component 12. One then has direct access to the blood serum or plasma 50 and may be canted without remixing the blood serum or plasma 50 with substantially cellular portion 52. This is so because the thixotrope 36 is in a substantially rigid condition (no stress being applied to the thixotrope 36). Alternatively, if one desires to transfer blood serum or plasma 50 with a minimum of contact to the atmosphere, snap cap 32 may be removed and the blood serum or plasma 50 removed from chamber 21 by inserting a pipette through aperture 30. This is, of course, a preferred and convenient method when one desires minimal contact of the blood serum or plasma 50 with atmospheric gases or contaminants.

What is claimed:

1. Apparatus for the collection, separation and isolation of serum or plasma from capillary blood, which comprises;
   a. a first tubular body having a fixedly closed end and an open end, said open end having a greater width than said closed end, said body and said open and closed ends together defining a blood collection reservoir with the capacity of from about 200 to about 1,000 microliters of blood;
   b. a first flange disposed about the outer periphery of said open end;
   c. a movable first closure member adapted to nest in and to seal said open end, said closure member comprising;
      i. a second tubular body having open upper and lower ends and which defines a sealant holding chamber, the opening in said lower end being of a dimension which is insufficient to permit the passage of a thixotrope under the force of one gravity but sufficient to permit the passage of said thixotrope under a centrifugal force;
      ii. a second flange disposed about the outer periphery of said upper end;
      iii. a second movable closure member for sealing said upper end, said second movable closure having means formed therein for releasably engaging said second flange in a fluid tight sealing association;
      iiii. a thixotrope sealant held in said sealant chamber, said thixotrope having a specific gravity within the range of from 1.03 to 1.09;
   d. means formed on said second flange for releasably engaging said first flange in a fluid tight association; and
   e. means of movably attaching said first closure to said first tubular body; whereby when both of said means for releasably engaging said second flange are engaged, the contents of said apparatus are hermetically sealed therein.

2. The apparatus of claim 1 wherein said means formed on said second flange is an integrally molded lip.

3. The apparatus of claim 1 wherein said means (e) is an integrally molded strap hinge.

* * * * *